United States Patent
Haider et al.

(10) Patent No.: US 8,764,662 B2
(45) Date of Patent: Jul. 1, 2014

(54) ULTRASOUND IMAGING SYSTEM AND METHOD FOR TEMPERATURE MANAGEMENT

(75) Inventors: Bruno Hans Haider, Ballston Lake, NY (US); Krishnakumar Sundaresan, Clifton Park, NY (US); Boris Constantine Joesaar, Berlin (DE)

(73) Assignee: General Electric Company, Niskayuna, NY (US)

(*) Notice: Subject to any disclaimer, the term of this patent is extended or adjusted under 35 U.S.C. 154(b) by 0 days.

(21) Appl. No.: 13/537,109

(22) Filed: Jun. 29, 2012

(65) Prior Publication Data

US 2014/0005546 A1    Jan. 2, 2014

(51) Int. Cl.
  *A61B 8/00*    (2006.01)
  *A61B 8/14*    (2006.01)
  *G01K 1/00*    (2006.01)

(52) U.S. Cl.
  USPC ............................ 600/447; 600/459; 702/132

(58) Field of Classification Search
  USPC ............ 600/447, 459, 443; 604/22; 702/130, 702/132; 606/32, 41
  See application file for complete search history.

(56) References Cited

U.S. PATENT DOCUMENTS

| | | |
|---|---|---|
| 5,685,839 A | 11/1997 | Edwards et al. |
| 6,511,478 B1 | 1/2003 | Burnside et al. |
| 6,542,846 B1 | 4/2003 | Miller et al. |
| 6,908,434 B1 | 6/2005 | Jenkins et al. |
| 7,303,530 B2 | 12/2007 | Barnes et al. |
| 2005/0228284 A1 | 10/2005 | Baumgartner et al. |
| 2006/0004290 A1 | 1/2006 | Smith et al. |
| 2008/0281206 A1 | 11/2008 | Bartlett et al. |
| 2011/0060225 A1* | 3/2011 | Cogan et al. .................. 600/459 |

FOREIGN PATENT DOCUMENTS

| | | |
|---|---|---|
| JP | 2006175208 A | 7/2006 |
| WO | 2008146208 A2 | 12/2008 |

* cited by examiner

*Primary Examiner* — Michael Rozanski
(74) *Attorney, Agent, or Firm* — Scott J. Asmus

(57) ABSTRACT

A temperature management system and a method of monitoring temperature in an ultrasound imaging system is provided. The system includes an ultrasound probe. The ultrasound probe includes at least one ultrasound transducer and a plurality of application specific integrated circuits. Further, the system includes at least one temperature sensing device disposed on at least one of the plurality of application specific integrated circuits. The temperature sensing devices are disposed in such a way that the sensing devices are in thermal contact with at least one heat producing region of the ultrasound probe.

21 Claims, 4 Drawing Sheets

ULTRASOUND IMAGING SYSTEM AND METHOD FOR TEMPERATURE MANAGEMENT

BACKGROUND

The present invention relates, generally, to the field of ultrasound imaging systems, and specifically, to a temperature control system and method for ultrasound imaging systems.

Ultrasound imaging is used in medical diagnostics as a non-invasive imaging mechanism for soft tissue organs. An ultrasound imaging system typically includes a handheld ultrasound probe that is communicably coupled with a processor and a display screen. The ultrasound imaging technique involves placement of the ultrasound probe on a patient's body near a region of interest. For example, to capture images of the pancreas the ultrasound probe may be placed on the abdomen of the patient. The ultrasound probe holds an ultrasound transducer that transmits ultrasound energy into the patient's body through the region of interest. The transducer detects echoes of the ultrasound sound energy from the patient's body and transfers this detected data to the processor. The processor analyzes parameters of the echo of the ultrasound energy and creates a 2-dimensional image of the region of interest. The image is displayed on the display screen to allow a doctor/attendant to analyze the state of the region of interest. The ultrasound probe further holds application specific integrated circuits (ASICs) required for, among other activities, generating control signals to transmit ultrasound energy, receiving ultrasound energy.

With improvements in technology it is now possible to obtain 3-dimensional as well as 4-dimensional images from ultrasound probes. With the need to obtain precise and accurate images ultrasound probes now include at least one processing ASIC that aids in beamforming. The ASIC is communicably coupled with the ultrasound transducer and hence is operational when the probe is being used. During operation of the probe, due to high processing requirements, the transducer/ASIC combination has the highest temperature in the probe assembly. The heat generated in the probe can cause injuries to the patient, since the probe is in direct contact with the patient's body. The International Electrotechnical Commission (IEC) has defined a standard to ensure safety of patients being monitored and treated with medical electrical equipment. The standard (IEC-60601) has particularly defined that the temperature of the ultrasound probe should not exceed 43° C.

Current ultrasound probe temperature is measured using separate thermistors placed near a contact point of the ultrasound probe. One of the major disadvantages with the presence of separate thermistors is that the ultrasound operator is alerted after a considerable delay. Further, since the thermistors are bulky, they cannot be integrated with each of the multiple ASICs in modern day ultrasound probes. Further, the wiring required for thermistors is prone to failures. To avoid these problems, operators are generally cautious with operational range for ultrasound temperatures and generally start the cooling process/switch off the ultrasound probe even when the temperature is considerably lower than 43° C.

Hence, there is a need for an effective temperature detection system and mechanism that integrates with multiple heat producing components from the ultrasound probe and provides for accuracy that allows for the ultrasound probe to be used to its limits and all the processing powers of ASICs to be utilized for obtaining high quality ultrasound images.

BRIEF DESCRIPTION

According to one embodiment, an ultrasound imaging system is provided. The ultrasound imaging system includes at least one ultrasound probe. The ultrasound probe includes at least one ultrasound transducer and a plurality of application specific integrated circuits. Further, the ultrasound imaging system includes one or more temperature sensing devices. The temperature sensing devices are disposed on at least one of the plurality of application specific integrated circuits. Furthermore, the temperature sensing devices are disposed so as to be in thermal contact with one or more heat producing regions of the ultrasound probe.

According to another embodiment, an ultrasound imaging system is provided. The ultrasound imaging system includes at least one ultrasound probe. The ultrasound probe includes at least one ultrasound transducer, and a plurality of application specific integrated circuits (ASICs). Further, the ultrasound imaging system includes one or more temperature sensing devices. The temperature sensing devices are disposed on at least one of the plurality of ASICs to be in thermal contact with one or more heat producing regions of the ultrasound probe. Furthermore, the ultrasound imaging system includes a calibration circuit coupled to the one or more temperature sensing devices. The calibration circuit calibrates an output of the one or more temperature sensing devices based on determination of an error induced in the output of the temperature sensing devices.

According to yet another embodiment, a method for temperature management in an ultrasound imaging system is provided. The method includes disposing one or more temperature sensing devices proximate to one or more heat producing regions on a plurality of application specific integrated circuits (ASICs) of the ultrasound imaging system. Further, the method includes controlling operations of the ASICs based on an output of the one or more temperature sensing devices.

DRAWINGS

The present invention will be better understood from reading the following description of non-limiting embodiments, with reference to the attached drawings, wherein below:

DETAILED DESCRIPTION

Figure 1:
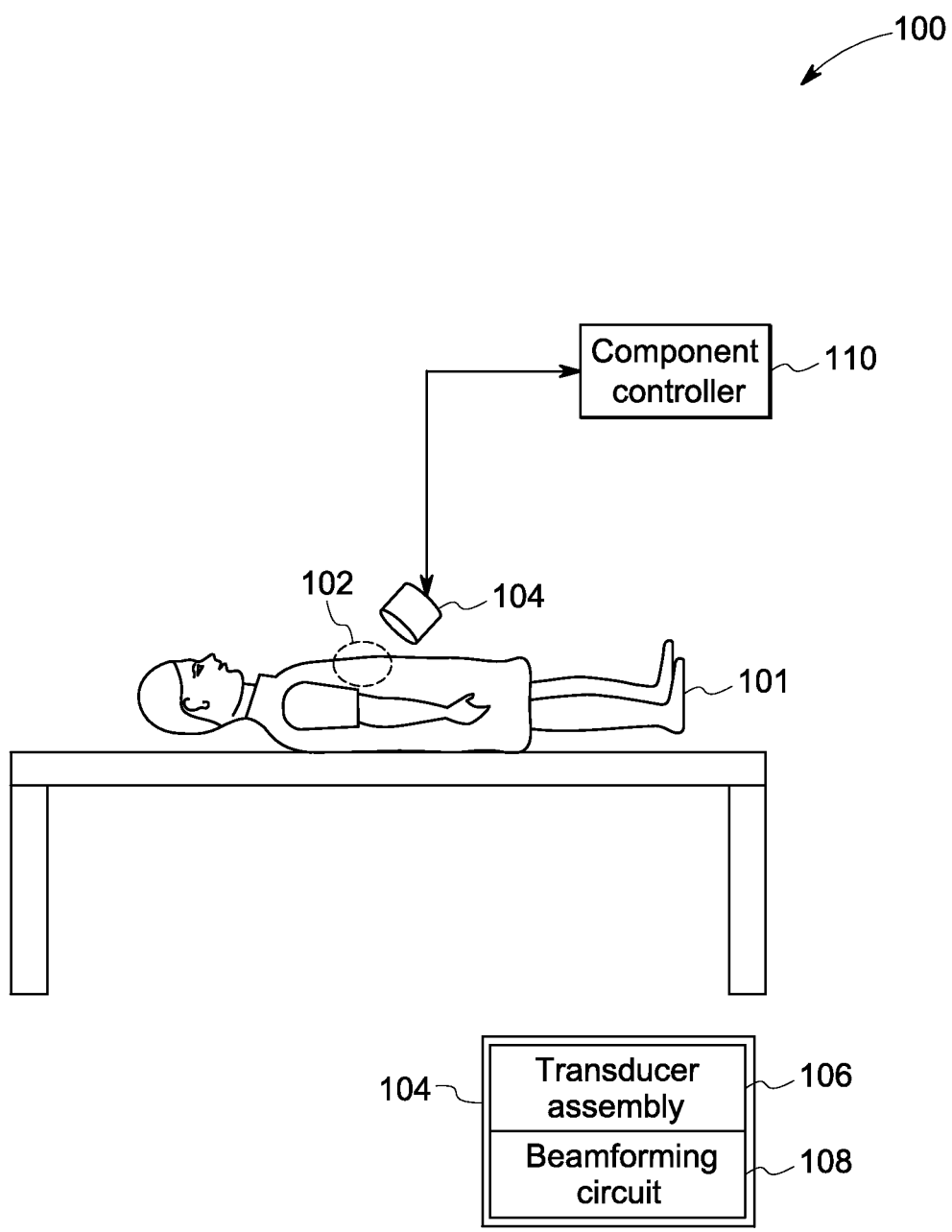
FIG. 1 illustrates a block diagram of an exemplary ultrasound imaging system.

Reference will be made below in detail to exemplary embodiments of the invention, examples of which are illustrated in the accompanying drawings. Wherever possible, the same reference numerals used throughout the drawings refer to the same or like parts.

FIG. 1 is a block diagram of an example of an ultrasound imaging system 100. The figures are for illustrative purposes and are not drawn to scale. The ultrasound imaging system 100 may be configured to non-invasively image a region of interest 102 via a probe 104. The region of interest 102 may be a one-dimensional, two-dimensional or a three dimensional region. The region of interest 102, having diseased tissue or adipose tissue, for example, is located inside a patient 101.

The probe 104 typically includes an ultrasound transducer assembly 106 and a plurality of application specific integrated circuits (ASICs). In one embodiment, the plurality of ASICs includes a beamforming circuit 108 that is operatively coupled to the transducer assembly 106. The ASICs include time-gain compression circuitry, and receive and transmit circuitry. The beamforming circuit 108 is controlled using a component controller 110. The beamforming circuit 108, in one embodiment, comprises a pulser, transmit/receive (TX/RX) switching module, a voltage controlled amplifier, a beamformer, and an analog-to-digital converter (ADC).

The transducer assembly 106 includes at least one ultrasound transducer configured to transmit ultrasound waves to the region of interest 102 and sense acoustic waves reflected from the region of interest 102. Multiple transducers are arranged to form a matrix of ultrasound transducers in the transducer assembly 106. In certain embodiments, the matrix of ultrasound transducers is divided into smaller groups and a beamforming ASIC is associated with each such smaller group. The plurality of beamforming ASICs work in parallel to energize the transducer assembly 106 and also receive an output from the transducer assembly 106. The transducer assembly 106 may employ a single channel or multiple channels for transmission.

The component controller 110 is operatively coupled to the beamforming circuit 108 to control the parameters of the ultrasound wave, such as a shape, size, or direction of the beam being generated by the transducer assembly 106. For example, the component controller 110 may instruct the beamforming circuit 108 to impart time delays on the transmission or reception circuitry for shaping the beam in a lateral direction. The probe 104, in certain embodiments, includes the component controller 110.

During operation, ultrasound signals are incident on the region of interest 102. Reflected signals from the region of interest 102 are received by the transducer assembly 106. The transducer assembly 106 converts the reflected signals into electric signals. The electric signals from the transducer assembly 106 are communicated to the receive circuitry. The receive circuitry is communicably coupled with the probe 104 through control signals passed by the component controller 110 to the T/R switching circuitry.

Further, the receive circuitry transfers the electric signals received by the ultrasound probe 104 to a processing module. The processing module receives creates an image based on the output of the transducer assembly 106. The ultrasound probe 104 and the processing module are typically connected to each other through coaxial cables, but they may also communicate with each other through wireless chips placed in the probe 104.

Figure 2:
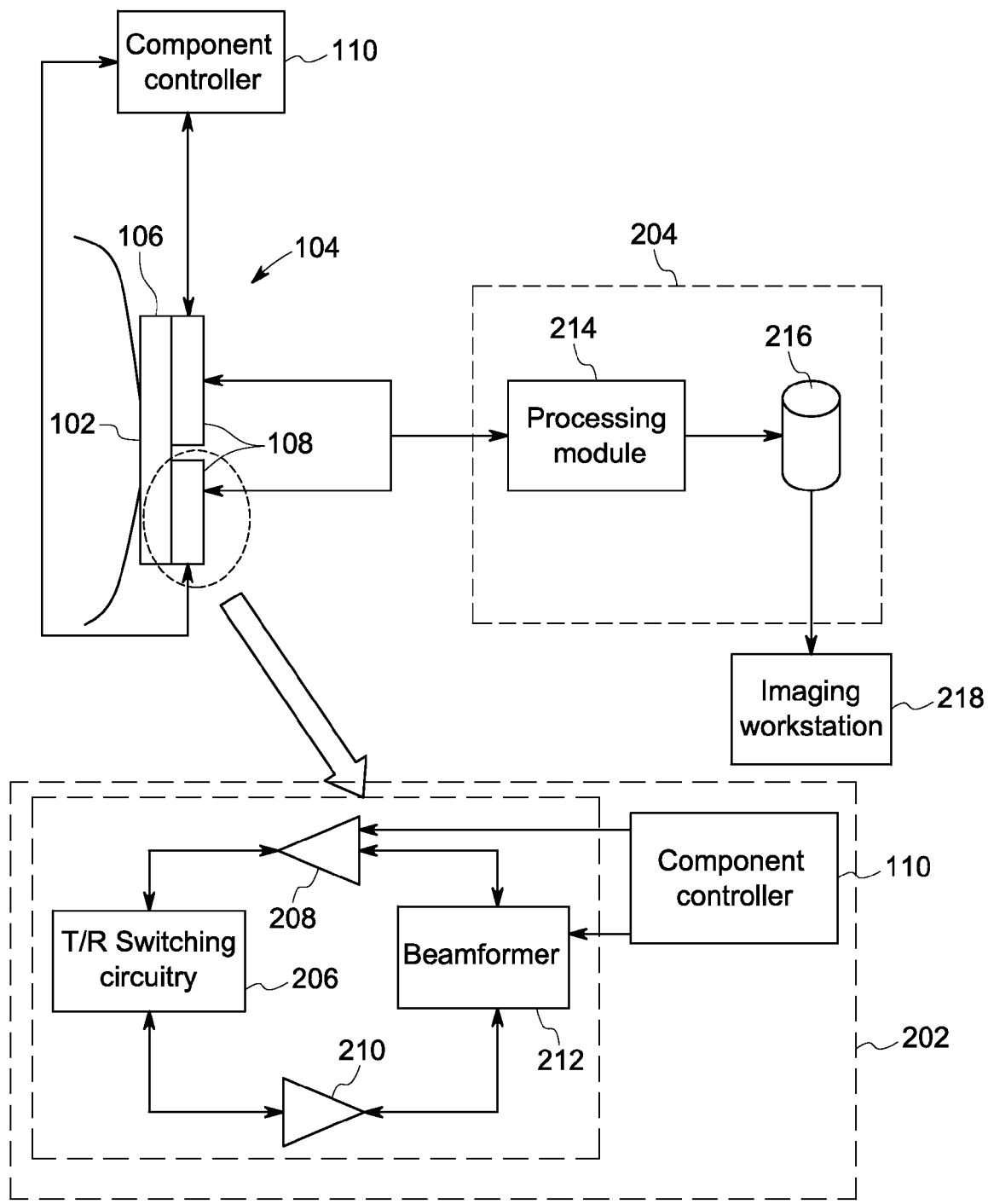
FIG. 2 illustrates a block diagram of an exemplary ultrasound probe in the ultrasound imaging system.

FIG. 2 illustrates a detailed block diagram of the ultrasound imaging system 100. The ultrasound probe 104 in the imaging system 100 includes the transducer assembly 106 and the beamforming circuit 108. In certain embodiments, as described above, the transducer assembly 106 is arranged in smaller groups. A group from the transducer assembly 106 is then coupled with one of a plurality of beamforming circuits 108 each. The circuitry associated with the ultrasound imaging system 100 can briefly be segmented into two sub-segments, an acquisition subsystem 202 and a processing subsystem 204. In the illustrated embodiment, the beamforming circuit 108 is included in the acquisition subsystem 202.

The acquisition subsystem 202 further includes the component controller 110 for controlling operations of the beamforming circuit 108. The beamforming circuit 108 also includes transmit/receive switching circuitry 206, a transmitter 208, and a receiver 210 and a beamformer 212. Transducers form the transducer assembly 106 convert the ultrasound energy from the acoustic waves reflected from the patient 101 into electrical signals. The electrical signals are then routed through the T/R switching circuitry 206 to the receiver 210. The received signals from the receiver 210 are provided to the beamformer 212 that performs beamforming and outputs a signal. The signal from the beamformer 212 is then provided to a processing module 214 that processes the signals. The receiver 210 amplifies the received signals and provides other functions such as gain compensation. The received signals, corresponding to the reflected acoustic waves, are received, by the transducer from the transducer assembly 106 at various times, and preserve the amplitude and phase information of the reflected waves. In certain embodiments, the component controller 110 is housed in the probe 104.

The ultrasound imaging system 100 transmits ultrasound energy into the patient 101 to treat and/or image the region of interest, and receives and processes reflected ultrasound signals from the patient 101 to create and display an image. To generate a transmitted wave of ultrasound energy, the component controller 110 sends command data to the beamforming circuit 108 to generate transmit parameters to create a wave of a desired shape originating from a certain point at the surface of the transducer assembly 106 at a desired steering angle. The component controller 110 also communicates with a focusing element to focus the ultrasound energy in the right direction and to adjust the steering angle. The transmitter 208 uses the transmission parameters to properly encode the signals to be sent to the transducer assembly 106 through the T/R switching circuitry 206. The signals are set at certain levels and phases with respect to each other and are transmitted to ultrasound transducer(s) of the transducer assembly 106. The transmitted signals excite the ultrasound transducer(s) to emit ultrasound waves with the same phase and level relationships. As a result, a transmitted wave of ultrasound energy is directed at the region of interest 102 along a scan line when the transducer assembly 106 is acoustically coupled to the region of interest 102 by using, for example, ultrasound gel.

The transmitted wave of ultrasound energy is passed through the region of interest 102 in the patient 101. The acoustic waves are back-scattered from physiological structures in the body, for example, adipose tissue, muscular tissue, blood cells, veins or objects within the body (e.g., a catheter or needle) to produce reflections that return to the transducer assembly 106. These reflections are received by the ultrasound transducer(s) in the transducer assembly 106 and passed to the receiver 210 for imaging purposes. The received reflections are provided to the processing subsystem 204, where processing module 214 processes the signals. The data may be transmitted to a memory 216 for storage (e.g., temporary or permanent storage).

Optionally, the memory 216 may be coupled to an imaging workstation 218. The processing subsystem 204 can be coupled to an imaging workstation through a wired connection. Alternatively, the processing subsystem 204 can be coupled with the imaging workstation 218 through a wireless connection. The components may be dedicated hardware elements such as circuit boards with digital signal processors or may be software running on a general-purpose computer or processor such as a commercial, off-the-shelf personal computer (PC). In the ultrasound imaging system 100, the acquisition sub-system 202 and the processing sub-system 204 are connected to each other through means of a wired connection. Data is transferred from the acquisition sub-system 202 to the processing sub-system through co-axial cables. In certain embodiments, the acquisition sub-system 202 and the processing sub-system 204 are connected to each other through a wireless connection.

In certain embodiments of the present invention, for example in a handheld ultrasound imaging system 100, the acquisition subsystem 202 and the processing subsystem 204 are disposed in the ultrasound probe 104. The processing subsystem 204 in such cases is implemented in the form of ASICs that are placed in the probe housing and receive signals and information from other ASICs in the probe assembly to output the ultrasound image obtained from reflected signals.

During operation, the acquisition subsystem 202 and the processing subsystem 204 generate heat which gets propagated in the probe 104 through various heat transfer mediums in the probe 104. The heat dissipated increases the temperature of the probe 104, both at, the location where an operator is holding the ultrasound probe 104, and the point of contact of the probe 104 with the patient 101. The temperature for this configuration needs to be maintained to ensure that injuries are not caused to both, the operator and the patient 101.

Figure 3:
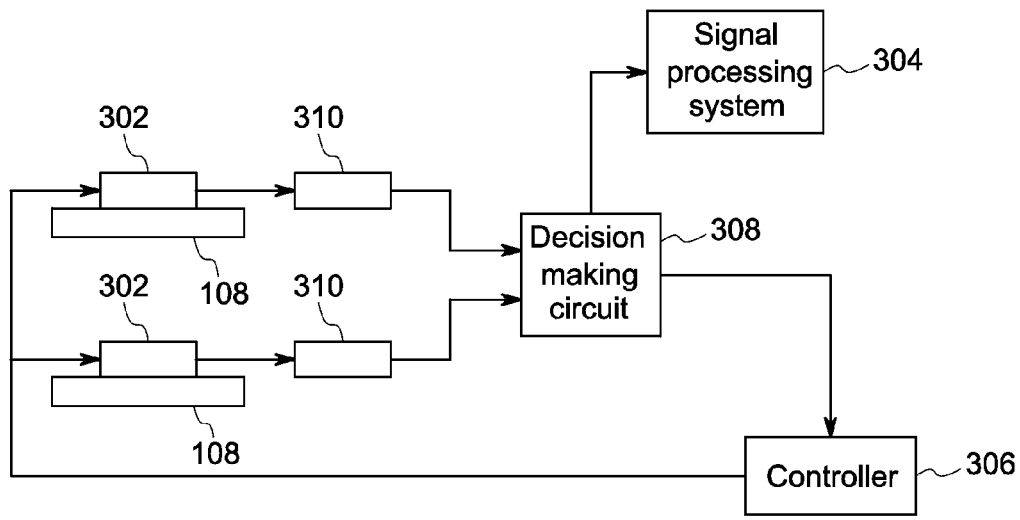
FIG. 3 illustrates a block diagram of a temperature management system in the ultrasound imaging system 100, according to one embodiment.

FIG. 3 illustrates a block diagram of the ultrasound imaging system 100 with temperature management system 300, according to one embodiment of the present invention. The temperature management system 300 includes at least one temperature sensing device 302 disposed on at least one of the plurality of application specific integrated circuits in the ultrasound imaging system 100. The temperature sensing devices 302 are disposed to be in thermal contact with one or more heat producing regions of the ultrasound probe 104 of the ultrasound imaging system. For example, in FIG. 3, the temperature sensing device 302 is disposed proximate the beamforming circuit 108 that produces heat in the probe 104.

The temperature sensing devices, in one embodiment, are sensors embodying bipolar semiconductor devices like diodes, and transistors. The temperature sensing devices 302 are selected such that they exhibit a linear voltage-temperature relationship. In certain embodiments one temperature sensing device 302 is placed proximate the heat producing regions to monitor temperature of the probe 104. In other embodiments, an array formed out of multiple temperature sensing devices 302 is placed to cover multiple heat producing regions in the probe 104. Temperature sensing devices integrated in the ASICs measure temperature at locations that were inaccessible to traditional temperature sensing devices used in probes 104. According to certain embodiments, the temperature sensing device 302 is integrated in at least one of the plurality of ASICs, during fabrication of the ASIC. The compact nature of the temperature sensing device 302 allows for placement of these devices on the ASIC without significantly increasing the size of the ASICs.

Each of the temperature sensing devices 302 outputs an electric signal that can be analyzed to determine the actual temperature of the heat producing regions of the ultrasound probe 104. The outputs of the temperature sensing device 302, in one embodiment, is amplified by an amplifier and then transmitted to a signal processing system 304. In one embodiment, the amplifier is the voltage controlled amplifier in the beamforming circuit 108. The signal processing system 304 analyzes the signals received from the temperature sensing device to generate a report on temperatures observed on the heat producing regions of the ultrasound probe 104. For example, the signal processing system 304 generates a 2-dimensional graph displaying amplitudes of electric signals outputted by the sensing devices 302. An operator observes this graph on a display system and can raise an alert for the probe 302 when the temperature exceeds a predefined threshold. Further, the signal processing system 304 may utilize the predefined threshold to display an alert on the display system for the operator to take appropriate actions. Furthermore, in case of handheld ultrasound imaging systems, the output of the sensing device 302 is analyzed by the signal processing system 304 integrated in the probe 104, and an alert is generated on body of the probe 104 when the temperature exceeds a predefined threshold.

Further, in certain embodiments, the ultrasound imaging system 100 includes a controller 306, configured to control operations of the ultrasound probe 104 and the plurality of ASICs integrated in the probe 104 in response to the output of the sensing devices 302. The controller 306, in one embodiment, switches off the ultrasound probe 104 when the temperature measured by any of the temperature sensing devices 302 exceeds the predefined threshold. Furthermore, the controller 306 is also configured to activate a cooling system to actively cool the ultrasound probe 104 while the probe 104 is being used. According to certain embodiments, the functions of the controller 306 are integrated in the component controller 110 that is communicably coupled with the ultrasound probe 104.

In case of multiple temperature sensing devices 302, the outputs of each of the multiple temperature sensing devices 302 are coupled with a decision making circuit 308. The decision making circuit 308, in one embodiment, can transmit the highest of all the temperatures observed by the multiple sensing devices 302 to the signal processing system. In another embodiment, the decision making circuit 308 is configured to transmit an average of all temperatures observed by the multiple temperature sensing devices 302. In yet another embodiment, the decision making circuit 308 is controlled by the component controller 110 to transmit a specific one of all temperatures observed by the multiple temperature sensing devices 302. The decision making circuit 308, in certain embodiments, performs statistical operations on the outputs of the temperature sensing devices 302 and transmits an output of the statistical operation to the signal processing system 304 and/or the controller 306.

Figure 4:
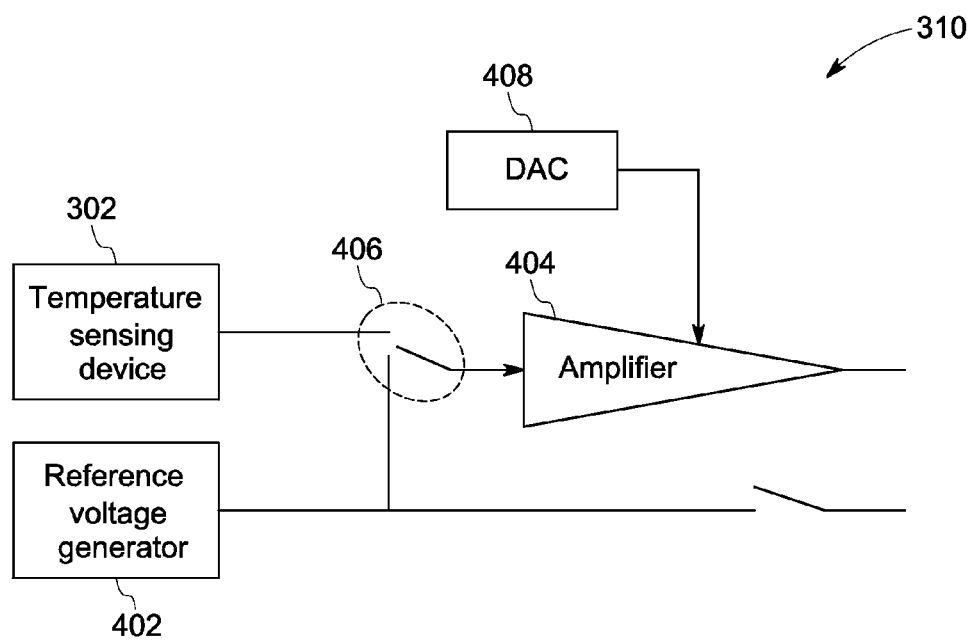
FIG. 4 illustrates a block diagram of a calibration circuit in the temperature management system, according to one embodiment.

Due to integration during fabrication, an error may be induced in the temperature sensing device 302. In one embodiment of the present invention, a calibration circuit 310 is provided to calibrate an output of the temperature sensing device 302 based on determination of the error induced in the sensing device 302 by the ASIC. A detailed view of the calibration circuit is provided in FIG. 4. During manufacture of the ASIC, a switch 406 from the calibration circuit 310 couples a reference voltage generator 402 and the temperature sensing device 302 to an amplifier 404. The amplifier 404, as described above, is the amplifier that amplifies the output of the sensing device 302. The amplifier 404, in turn is electrically coupled with the signal processing system 304 and/or the controller 306. During calibration, the switch 406 toggles to connect the reference voltage generator 402 to the amplifier 404. The reference voltage generator 402 is configured to supply voltage corresponding to the voltage generated by the temperature sensing device 302 in response to temperature equal to a predefined value. Since the amplification factor of the amplifier 404 is known, the output expected from the amplifier 404 is calculated. Actual output of the amplifier 404 is measured and stored in a non-volatile programmable memory. When the actual output of the amplifier is not equal to the expected output from the amplifier, a digital-to-analog converter (DAC) 408 is employed to provide for a correction signal that corrects the error induced by the amplifier in the voltage measurements. The correction signal provided by the DAC 408 is then stored in the programmable memory of the ultrasound probe 104.

During operation of the ultrasound probe 104, the correction signal values stored for the reference voltage are utilized when the temperature sensing devices 302 provide output voltages. The correction signal corrects the output provided by the temperature sensing devices 302 in accordance with the error induced in the output during the manufacture of the temperature sensor integrated ASIC.

In another embodiment, during operation of the ultrasound probe 104, the voltage output of the amplifier 404 corresponding to the reference temperature measured by the temperature sensing device 302 is compared to the actual output of the amplifier 404 for the reference voltage that is stored in the programmable memory of the probe 104. If the voltage output for the reference temperature is different from the actual output of the amplifier, the DAC 408 provides correction signal to converge the two outputs to the same value.

Figure 5:
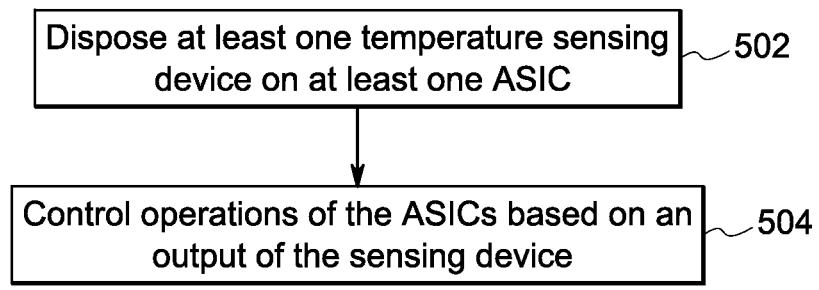
FIG. 5 is a flow chart representing a method for temperature management in an ultrasound imaging system, according to another embodiment.

FIG. 5 is flow chart illustrating a method for temperature management of the ultrasound imaging system 100. The method includes, at step 502, disposing at least one temperature sensing device 302 on at least one of the plurality of ASICs in the ultrasound probe 104. At step 504, the operations of the plurality of ASICs are controlled based on an output of the at least one temperature sensing device 302.

In one embodiment, the step of controlling operations of the plurality of ASICs includes switching off power supply to the plurality of ASICs when the output of at least one temperature sensing devices 302 exceeds a predefined threshold. Further, the step of controlling also includes switching on a cooling system for the ultrasound probe 104 when the temperature of the probe 104 exceeds the predefined threshold.

In one embodiment, the method also includes the step of calibrating output of the at least one temperature sensing device 302 based on a determination of error induced in the output of the at least one temperature sensing device 302 by the ASICs, prior to operation of the ultrasound probe 104. The step of calibrating further includes applying a reference voltage to the amplifier 404 that amplifies the output of the at least one temperature sensing device 302. The output of the amplifier 404 corresponding to the reference voltage is stored in a non-volatile programmable memory of the ultrasound probe 104. Expected output for the reference voltage is calculated based on an amplification factor of the amplifier 404 in the calibration circuit. The method further includes the step of providing a correction signal to the amplifier when the actual output of the amplifier for the reference voltage is different from the expected output of the amplifier for the reference voltage. The correction signal, provided by the DAC 408, is equal to the difference between the actual output and the expected output.

Various embodiments discussed herein provide for a method and system for temperature management in an ultrasound imaging system. The integrated temperature management system reduces cost of the ultrasound imaging system by eliminating the need of separate thermistors for the plurality of ASICs in the imaging system. Further, the calibration circuit as per the above description provides for accurate results that help the operator in utilizing the ultrasound imaging system till the time the temperatures reach closer to the predefined threshold. The ultrasound imaging system can thus be used for more complex imaging and signal processing.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable any person of ordinary skill in the art to practice the embodiments of invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described the ultrasound imaging system, without departing from the spirit and scope of the invention herein involved, it is intended that all of the subject matter of the above description or shown in the accompanying drawings shall be interpreted merely as examples illustrating the inventive concept herein and shall not be construed as limiting the invention.

The invention claimed is:

1. An ultrasound imaging system comprising:
   at least one ultrasound probe, wherein the ultrasound probe comprises at least one ultrasound transducer and a plurality of application specific integrated circuits;
   one or more temperature sensing devices disposed on at least one of the plurality of application specific integrated circuits such that the temperature sensing devices are in thermal contact with one or more heat producing regions of the ultrasound probe; and
at least one calibration circuit coupled with the one or more temperature sensing devices, the calibration circuit comprising:
a voltage amplifier;
a reference voltage generator configured to provide reference voltage input to the voltage amplifier, wherein the reference voltage input corresponds to voltage expected to be generated by the temperature sensing device in response to temperature of a predefined value;
a switch configured to couple either the one or more temperature sensing devices or the reference voltage generator with the voltage amplifier; and
a digital-to-analog converter configured to provide a correction signal to the voltage amplifier based on an error between an output generated by the voltage amplifier for the reference voltage input and output generated by the voltage amplifier for an output of the one or more temperature sensing devices in response to the temperature of the predefined value.

2. The ultrasound imaging system as recited in claims 1, wherein the plurality of application specific integrated circuits comprises a beam-forming integrated circuit.

3. The ultrasound imaging system as recited in claim 1, wherein the temperature sensing devices exhibit a voltage-temperature relationship.

4. The ultrasound imaging system as recited in claim 1, wherein the one or more heat producing regions are proximate the plurality of application specific integrated circuits.

5. The ultrasound imaging system as recited in claim 1 further comprises a signal processing system coupled with the one or more temperature sensing devices to analyze the output of the temperature sensing device.

6. The ultrasound imaging system as recited in claim 1 further comprises a controller configured to control operations of the plurality of application specific integrated circuits in response to an output from the one or more temperature sensing devices.

7. The ultrasound imaging system as recited in claim 6 further comprises a decision making circuit, wherein the decision making circuit is configured to select which output of the at least one or more temperature sensing devices is transmitted to the controller.

8. The ultrasound imaging system as recited in claim 6 wherein the controller is configured to trigger an alert for the ultrasound probe, when the output of at least one of the one or more temperature sensing devices exceeds a predefined threshold.

9. The ultrasound imaging system as recited in claim 8, wherein the controller is configured to trigger the alert based on a statistical operation performed on the outputs of the one or more temperature sensing devices.

10. The ultrasound imaging system as recited in claim 1 further comprises a memory to store the correction signal corresponding to the at least one ultrasound probe.

11. The ultrasound imaging system as recited in claim 1, wherein the correction signal is calculated at a time of manufacture of the ultrasound imaging system.

12. An ultrasound imaging system comprising:
at least one ultrasound probe, wherein the ultrasound probe comprises at least one ultrasound transducer and a plurality of application specific integrated circuits;
one or more temperature sensing devices disposed on the plurality of application specific integrated circuits thermally coupled with one or more heat producing regions of the ultrasound probe; and
a calibration circuit coupled to the one or more temperature sensing devices, wherein the calibration circuit further comprises:
a voltage amplifier;
a reference voltage generator configured to provide reference voltage input to the voltage amplifier, wherein the reference voltage input corresponds to voltage expected to be generated by the temperature sensing device in response to temperature of a predefined value;
a switch configured to couple either the one or more temperature sensing devices or the reference voltage generator with the voltage amplifier; and
a digital-to-analog converter configured to provide a correction signal to the voltage amplifier based on an error between an output generated by the voltage amplifier for the reference voltage input and output generated by the voltage amplifier for an output of the one or more temperature sensing devices in response to the temperature of the predefined value.

13. The ultrasound imaging system as recited in claim 12 further comprises a controller configured to control operations of the plurality of application specific integrated circuits in response to an output from at least one of the one or more temperature sensing devices.

14. The ultrasound imaging system as recited in claim 13 further comprises a decision making circuit, wherein the decision making circuit is configured to select which output of the at least one of the one or more temperature sensing devices is transmitted to the controller.

15. The ultrasound imaging system as recited in claim 13 wherein the controller is configured to trigger an alert for the ultrasound probe, when the output of at least one of the one or more temperature sensing devices exceeds a predefined threshold.

16. The ultrasound imaging system as recited in claim 15, wherein the controller is configured to trigger the alert based on a statistical operation performed on the outputs of the one or more temperature sensing devices.

17. The ultrasound imaging system as recited in claim 12 further comprises a signal processing system coupled with the one or more temperature sensing devices to analyze an output of the temperature sensing device.

18. A method for temperature management of an ultrasound imaging system, the method comprising:
disposing one or more temperature sensing devices on a plurality of application specific integrated circuits of the ultrasound imaging system;
controlling operations of the plurality of application specific integrated circuits based on an output of at least one of the one or more temperature sensing devices;
comparing an expected output for a temperature of predefined value with an actual output of the one or more temperature sensing devices to the temperature of predefined value; and
calibrating the output of the one or more temperature sensing devices based on the comparison, wherein calibrating comprises applying a correction signal corresponding to the comparison to the one or more temperature sensing devices.

19. The method for temperature management as recited in claim 18 further comprises storing the correction signal in a memory associated with the ultrasound imaging system.

20. The method for temperature management as recited in claim 18 further comprises calculating the correction signal during manufacture of the ultrasound imaging system.

21. The method for temperature management as recited in claim 18 further comprises triggering an alert when the output of at least one of the one or more temperature sensing devices exceeds a predefined threshold.

* * * * *